(12) United States Patent
Ikeda

(10) Patent No.: US 6,541,741 B2
(45) Date of Patent: Apr. 1, 2003

(54) HEATER CONTROL DEVICE FOR AIR-FUEL RATIO SENSOR

(75) Inventor: Shinji Ikeda, Mishima (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 09/917,926

(22) Filed: Jul. 31, 2001

(65) Prior Publication Data

US 2002/0043460 A1 Apr. 18, 2002

(30) Foreign Application Priority Data

Aug. 24, 2000 (JP) ........................................ 2000-259375

(51) Int. Cl.⁷ .................... G01N 27/409; G01N 27/41
(52) U.S. Cl. .................... 219/492; 219/497; 204/402; 204/406; 204/408; 204/424; 123/697
(58) Field of Search ................ 204/401, 406, 204/408, 424, 425, 427, 402; 219/490, 492, 497; 123/697

(56) References Cited

U.S. PATENT DOCUMENTS

| 5,090,387 A | * | 2/1992 | Mayer et al. ............... 123/479 |
| 5,245,979 A | * | 9/1993 | Pursifull et al. ............ 123/690 |
| 5,669,219 A | * | 9/1997 | Schnaibel et al. .......... 123/697 |
| 5,758,310 A | * | 5/1998 | Kato ........................... 123/688 |
| 6,083,370 A |   | 7/2000 | Kato et al. |
| 6,205,989 B1 |  | 3/2001 | Aoki |
| 6,258,232 B1 | * | 7/2001 | Hasegawa et al. .......... 204/424 |
| 6,332,966 B1 | * | 12/2001 | Sakai et al. ................. 204/406 |

FOREIGN PATENT DOCUMENTS

| EP | 1 033 486 A2 | 9/2000 |
| JP | A 10-232220 | 9/1998 |
| JP | A 2000-46780 | 2/2000 |
| JP | A 2000-258387 | 9/2000 |

* cited by examiner

Primary Examiner—Robert J. Warden, Sr.
Assistant Examiner—Kaj K. Olsen
(74) Attorney, Agent, or Firm—Oliff & Berridge, PLC

(57) ABSTRACT

In performing control to supply power to a heater by detecting the impedance of a sensor element and feeding it back for control, a heater control device for an air-fuel ratio according to the invention can prevent damage to the heater or the sensor element by suppressing an excessive rise in the temperature of the heater and hence the sensor element even when the impedance of the sensor element has increased due to degradation of the sensor element. The heater control device includes: a feedback control unit which, based on the impedance of the air-fuel ratio sensor element, controls supply power to the heater for heating the air-fuel ratio sensor; a half-activation time detection unit which detects the half-activation time of the air-fuel ratio sensor; and a power limiting unit which, based on the half-activation time detected by the half-activation time detection unit, limits the power that is feedback-controlled by the feedback control unit.

1 Claim, 9 Drawing Sheets

HEATER CONTROL DEVICE FOR AIR-FUEL RATIO SENSOR

BACKGROUND OF THE INVENTION

1. Field of the Invention

The present invention relates to a heater control device for an air-fuel ratio sensor.

2. Description of the Related Art

To reduce both the fuel consumption and the amount of harmful gas emissions in an internal combustion automotive engine, the air-fuel ratio (A/F) of the mixture burned in the engine must be controlled over a wide range. To achieve such air/fuel control, an air-fuel ratio sensor having a sensor body constructed from an oxygen ion conducting element (sensor element), such as a zirconia solid electrolyte, with an electrode deposited on the reference atmosphere side and an electrode and a diffused resistor on the exhaust gas side, has been commercially implemented (this sensor is called a wide-range air-fuel ratio sensor or a linear air-fuel ratio sensor); this air-fuel ratio sensor detects the A/F ratio by utilizing the limiting current that is generated in proportion to the concentration of oxygen or unburned gas in the exhaust when a voltage is applied across the sensor body, and feedback control is performed based on the output of the air-fuel ratio sensor.

In performing air-fuel ratio feedback control based on the output of the wide-range air-fuel ratio sensor, it is indispensable to maintain the oxygen ion conducting element in an active state. For this purpose, control is performed to maintain the sensor element at a constant temperature by heating the element with a heater. At this time, the sensor element temperature needs to be detected but, since a correlation exists between the impedance and temperature of the sensor element, the need for a temperature sensor is eliminated as the sensor element temperature can be estimated by detecting the sensor element impedance (refer, for example, to Japanese Unexamined Patent Publication No. 10-232220 (corresponding U.S. Pat. No. 6,083,370)).

However, as the sensor element degrades over time, the element impedance becomes higher for the same element temperature. As a result, when the sensor element has degraded, if feedback control of heater supply power is performed so that the detected value of the element impedance matches the target impedance, the element temperature may rise even when there is no degradation in the output characteristic or response of the air-fuel ratio sensor, and the sensor can be damaged.

SUMMARY OF THE INVENTION

The present invention has been devised in view of the above problem, and an object of the invention is to provide a heater control device, for an air-fuel ratio sensor, that maintains the air-fuel ratio sensor in an active state by detecting the sensor element impedance of the air-fuel ratio sensor and feeding it back to control the power supplied to the heater wherein, even when the sensor element has degraded, damage to the heater or the sensor element is prevented by suppressing an excessive rise in the temperature of the heater and hence the sensor element.

To achieve the above object, according to the present invention, there is provided a heater control device for an air-fuel ratio sensor, comprising: feedback control means for controlling supply power to a heater, based on element impedance of the air-fuel ratio sensor, for heating the air-fuel ratio sensor; half-activation time detection means for detecting half-activation time of the air-fuel ratio sensor; and power limiting means for limiting, based on the half-activation time detected by the half-activation time detection means, the power that is feedback-controlled by the feedback control means.

In the thus configured heater control device for the air-fuel ratio sensor according to the present invention, the half-activation time, which reflects the degree of degradation of the sensor element, is detected before performing heater supply power control based on the feedback of the sensor element impedance, and the supply power at the time of feedback control is limited based on the thus detected half-activation time; this provides a reliable means to avoid situations where excessive power is supplied by feedback control to the sensor element whose impedance has increased due to degradation of the element, and the temperature of the heater and hence the sensor element rises excessively, resulting in damage to the heater or the sensor element.

BRIEF DESCRIPTION OF THE DRAWINGS

Further features and advantages of the present invention will be apparent from the following description with reference to the accompanying drawings, in which:

FIG. 7 is a time chart showing the variations of element temperature, heater energization duty ratio, and sensor output with the elapsed time from ignition switch-on;

DESCRIPTION OF THE PREFERRED EMBODIMENTS

An embodiment of the present invention will be described below with reference to the accompanying drawings.

Figure 1:
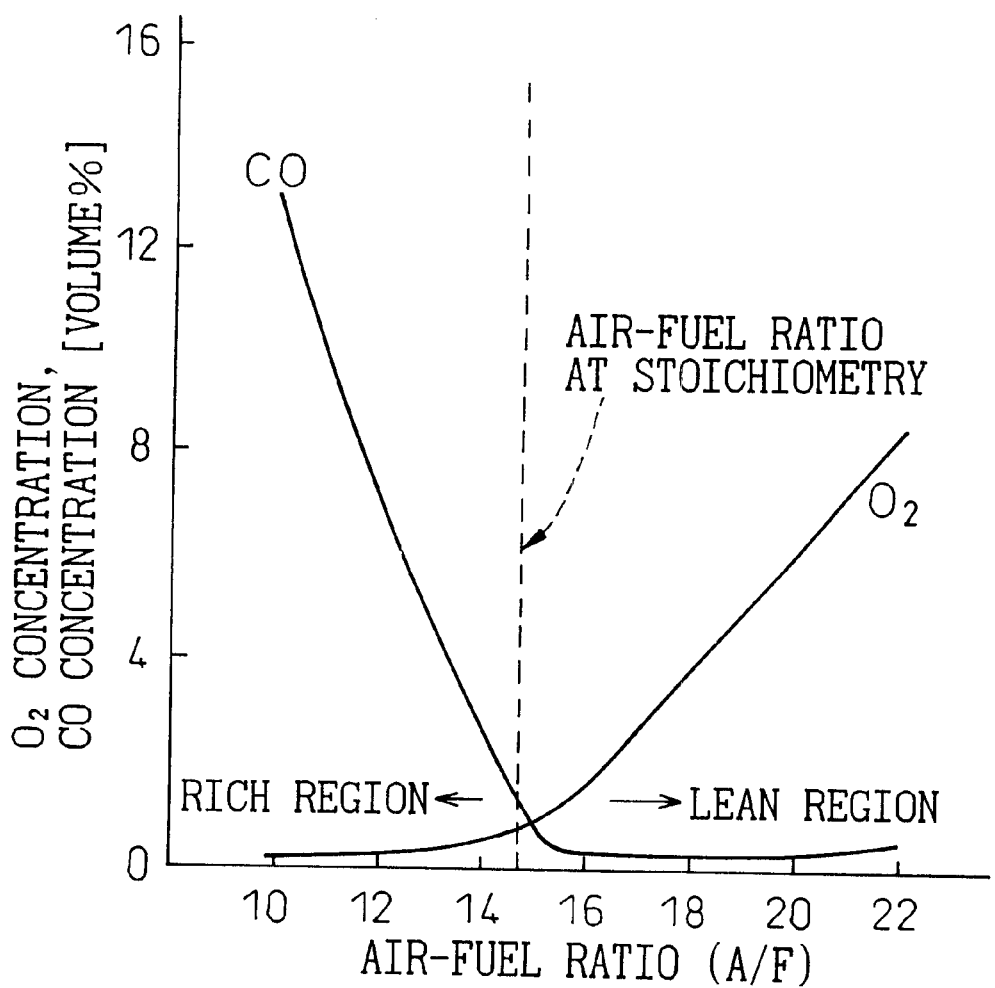
FIG. 1 is a characteristic diagram showing the relationship between the air-fuel ratio and the concentrations of exhaust gas constituents.

First, the basic principle of the air-fuel ratio sensor will be described. FIG. 1 is a characteristic diagram showing the relationship between the air-fuel ratio and the oxygen ($O_2$) concentration and carbon monoxide (CO) concentration in the exhaust gas. As shown in the diagram, in the air-fuel ratio region leaner than the stoichiometric air-fuel ratio, the $O_2$ concentration varies substantially linearly with the air-fuel ratio, while in the air-fuel ratio region richer than the stoichiometric air-fuel ratio, the concentration of CO as an unburned gas varies substantially linearly with the air-fuel ratio. The air-fuel ratio sensor uses this relationship, as will be described later.

Figure 2:
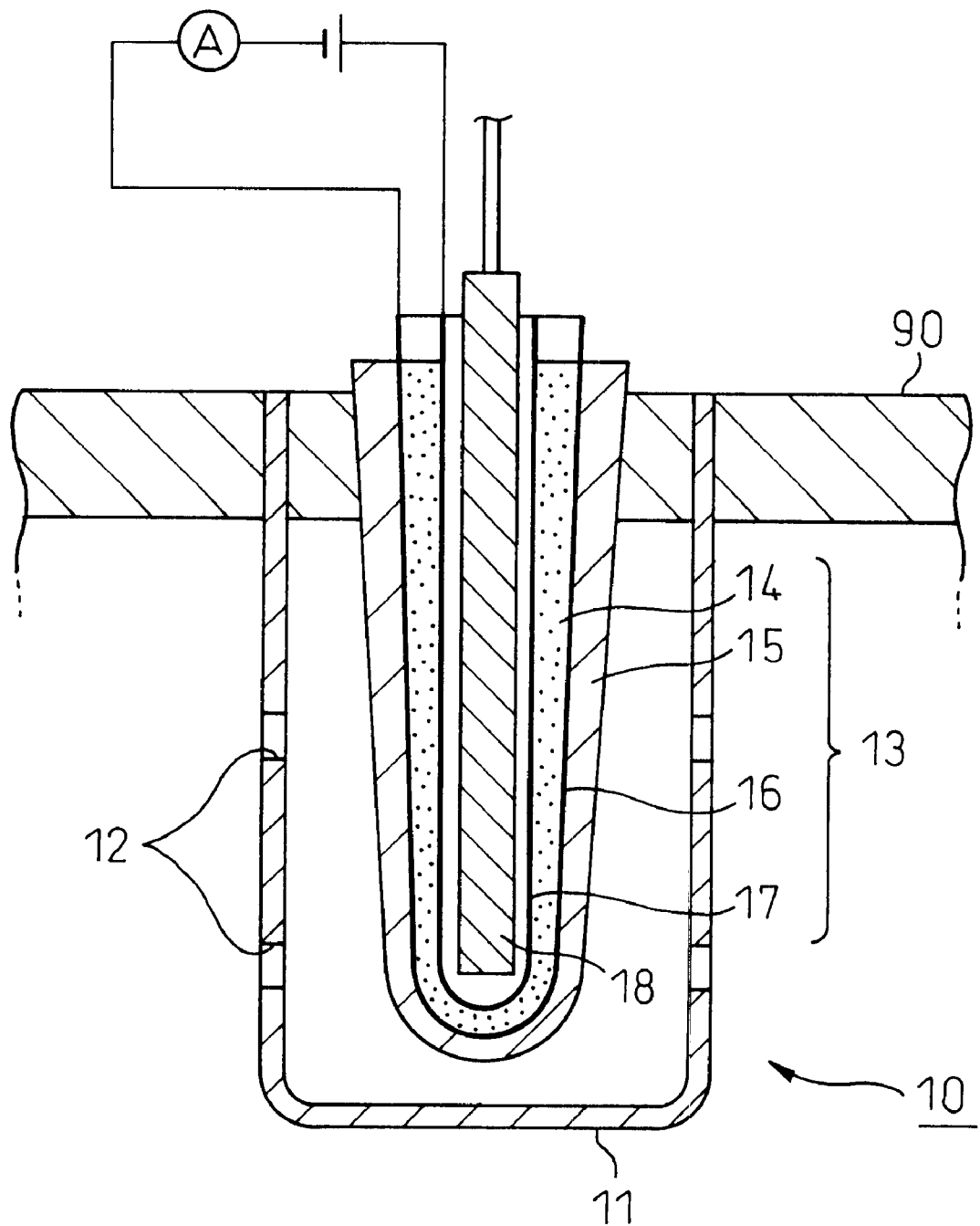
FIG. 2 is a cross-sectional view showing one example of the structure of an air-fuel ratio sensor.

FIG. 2 is a cross-sectional view showing one example of the structure of the air-fuel ratio sensor. The air-fuel ratio sensor 10 is mounted with its tip located inside an exhaust manifold 90 of an internal combustion engine. The air-fuel ratio sensor 10 consists essentially of a cover 11, a sensor main body 13, and a heater 18. The cover 11 has a U-shaped cross section, and numerous pores communicating between the interior and exterior of the cover are formed in its circumferential wall.

In the sensor main body 13, an exhaust-side electrode layer 16 is fixedly formed on the outside of an oxygen ion conducting solid electrolyte layer 14 formed in the shape of a test tube, while on the inside thereof is fixedly formed an atmosphere-side electrode layer 17. On the outside of the exhaust gas-side electrode layer 16 is formed a diffused resistor layer 15 by plasma spray coating or like means. In the present embodiment, the solid electrolyte layer 14 is formed, for example, from a sintered base of an oxygen ion conducting oxide, particularly a $ZrO_2$ (zirconia element) with CaO or the like added as a stabilizer in solid solution (hereinafter, the solid electrolyte layer 14 is also called the sensor element). The diffused resistor layer 15 is formed from a heat resistant inorganic material such as alumina. The exhaust-side electrode layer 16 and the atmosphere-side electrode layer 17 are both formed from a noble metal having high catalytic activation, such as platinum, and their surfaces are coated with porous chemical plating or the like.

The heater 18 is housed in a space surrounded by the atmosphere-side electrode layer 17, and activates the zirconia element 14 by heating the sensor main body 13 with its heat energy. The heater 18 has enough heating capacity to activate the zirconia element 14.

The zirconia element 14 has the characteristic that, when a difference in oxygen concentration occurs between both sides of the element in a high-temperature activated state, oxygen ions ($O^{2-}$) are passed from the higher concentration side to the lower concentration side (oxygen cell characteristic). The zirconia element 14 has the further characteristic that, when a potential difference exist between both sides of the element, the oxygen ions ($O^{2-}$) tend to move from the cathode to the anode in proportion to the magnitude of the potential difference (oxygen pumping characteristic).

As shown in FIG. 2, a predetermined bias voltage is applied across the sensor main body 13 with the atmosphere-side electrode layer 17 as the anode and the exhaust-side electrode layer 16 as the cathode. When the air-fuel ratio in the exhaust is lean, the movement of oxygen ions ($O^{2-}$) from the exhaust-side electrode layer 16 to the atmosphere-side electrode layer 17 occurs because of the oxygen pumping characteristic. As a result, a current flows from the positive terminal to the negative terminal of the bias voltage source through the atmosphere-side electrode layer 17, solid electrolyte layer 14, and exhaust-side electrode layer 16. The magnitude of the current flowing at this time is proportional to the amount of oxygen that flows by diffusion from the exhaust into the exhaust-side electrode layer 16 through the diffused resistor layer 15 when the bias voltage is set equal to or larger than the predetermined value. Accordingly, by detecting the magnitude of this limiting current, it is possible to determine the oxygen concentration and hence the air-fuel ratio in the lean region as explained with reference to FIG. 1.

On the other hand, when the air-fuel ratio in the exhaust is rich, the oxygen cell characteristic comes into play, causing the oxygen ions ($O^{2-}$) to tend to move from the atmosphere-side electrode layer 17 to the exhaust-side electrode layer 16. That is, the oxygen cell characteristic acts in the direction opposite to the bias voltage. Since the air-fuel ratio sensor is designed so that the electromotive force due to the oxygen cell characteristic overcomes the bias voltage, a current flows from the atmosphere-side electrode layer 17 to the exhaust-side electrode layer 16 through the bias voltage source. The magnitude of the current flowing at this time is determined by the amount of oxygen ions ($O^{2-}$) transported through the solid electrolyte layer 14 from the atmosphere-side electrode layer 17 to the exhaust-side electrode layer 16. Since the oxygen ions react (burn) on the exhaust-side electrode layer 16 with unburned gases, such as carbon monoxide, that flow by diffusion from the exhaust into the exhaust-side electrode layer 16 through the diffused resistor layer 15, the amount of oxygen ions transported is proportional to the unburned gas concentration. Accordingly, by detecting the magnitude of this limiting current, it is possible to know the unburned gas concentration and hence the air-fuel ratio in the rich region as explained with reference to FIG. 1.

When the air-fuel ratio in the exhaust is stoichiometric, since the amounts of the oxygen and unburned gases flowing into the exhaust-side electrode layer 16 are at the chemical equivalent ratio, both burn completely because of the catalytic action of the exhaust-side electrode layer 16. Accordingly, no oxygen remains in the exhaust-side electrode layer 16, resulting in the absence of oxygen ions to be transported by the oxygen cell or oxygen pumping characteristic. As a result, when the air-fuel ratio in the exhaust is at stoichiometry, no current flows in the circuit.

Figure 3:
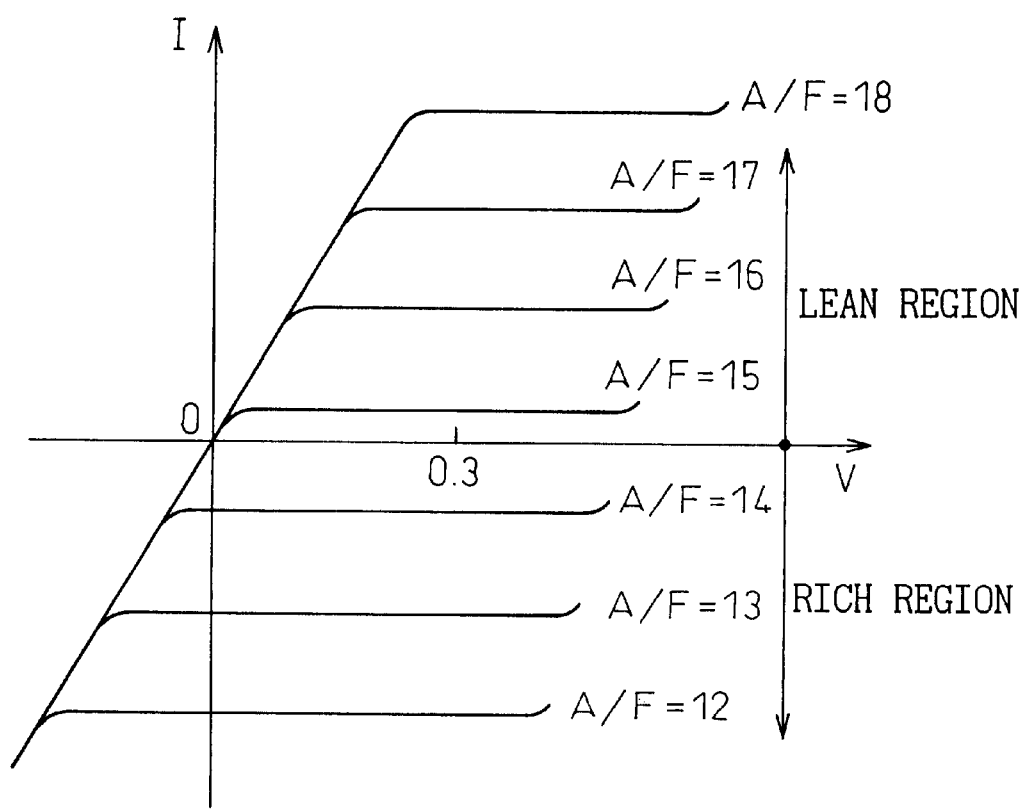
FIG. 3 is a characteristic diagram showing one example of the voltage-current characteristic of the air-fuel ratio sensor.

Thus, as shown in FIG. 3, the voltage-current (V-I) characteristic of the air-fuel ratio sensor shows the limiting current that is proportional to the air-fuel ratio (A/F) in the exhaust to which the sensor is exposed. In FIG. 3, each straight line parallel to the V axis indicates the limiting current. The direction of the limiting current flow is reversed between the lean and rich regions; in the lean region, the magnitude of the limiting current increases as the air-fuel ratio increases, while in the lean region, the magnitude increases as the air-fuel ratio decreases. As can be seen from the characteristic diagram of FIG. 3, when the applied voltage is set to about 0.3 V, the air-fuel ratio can be detected over a wide range. The region where the voltage is smaller in value than the voltage in the straight line region parallel to the V axis, is the resistance dominant region.

Figure 4:
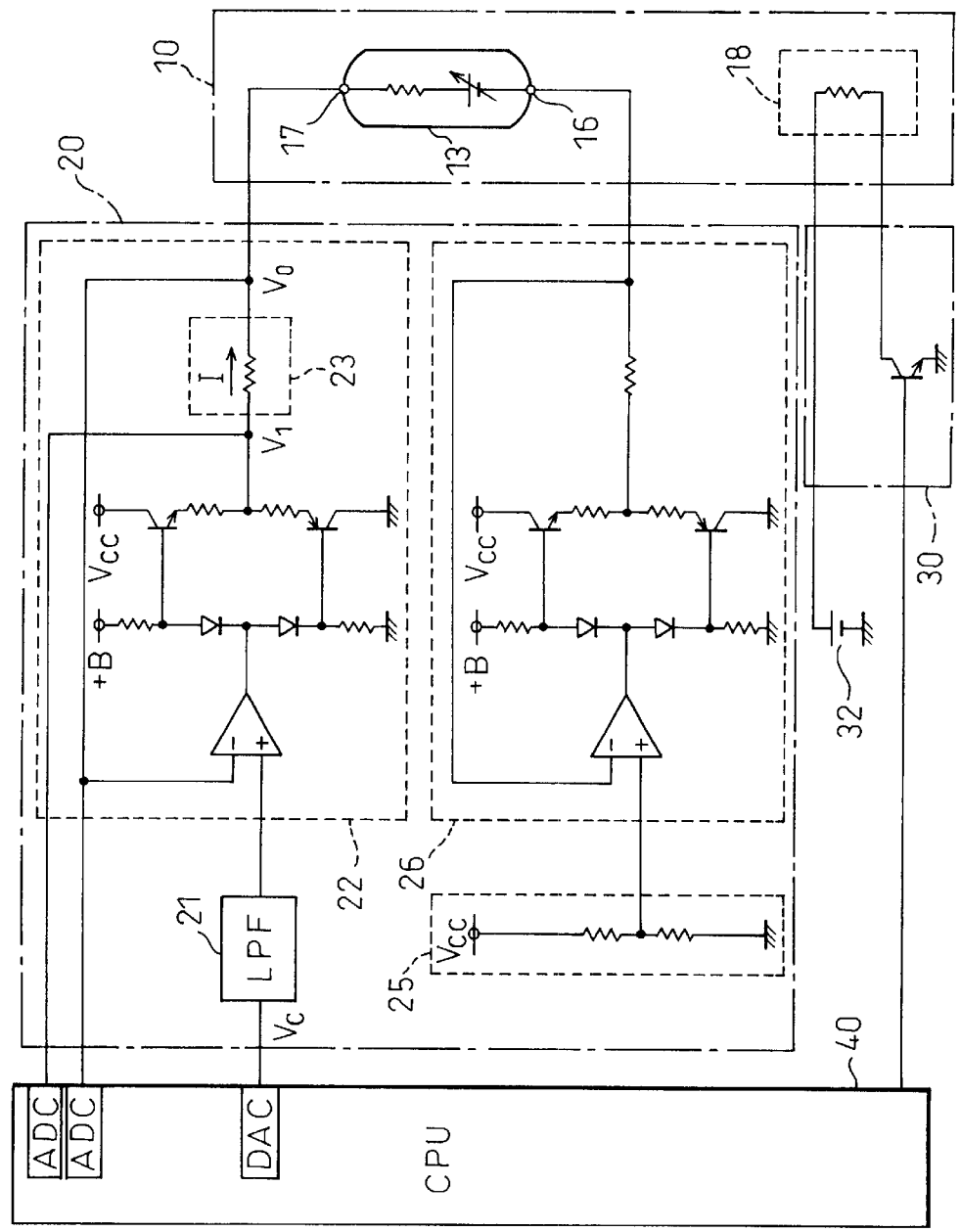
FIG. 4 is an electrical circuit diagram showing the hardware configuration of an air-fuel ratio detection device.

Next, one hardware configuration example of an air-fuel ratio detection device will be described with reference to FIG. 4. This air-fuel ratio detection device consists essentially of an air-fuel ratio sensor 10, a sensor main body driving circuit 20, a heater driving circuit 30, and a central processing unit (CPU) 40. The air-fuel ratio sensor 10 includes the sensor main body 13 and the heater 18, as explained with reference to FIG. 2. The heater driving circuit 30 receives a duty ratio signal, and applies a voltage from a battery 32 to the heater 18 in an ON/OFF fashion in accordance with the duty ratio. The CPU 40, the core of an electronic control unit (ECU) of an internal combustion engine, is responsible for fuel injection control, ignition timing control, etc. and contains an A/D converter (ADC), a D/A converter (DAC), and a memory. The CPU 40 also functions as a heater control device according to the present invention.

The sensor main body driving circuit 20 consists essentially of a low-pass filter (LPF) 21, a first voltage-follower circuit 22, a reference voltage generating circuit 25, and a second voltage-follower circuit 26. The LPF 21 removes high-frequency components from the analog signal voltage output from the CPU 40. The first voltage-follower circuit 22 comprises an operational amplifier, resistors, diodes, transistors, etc. and maintains the potential of the atmosphere-side electrode layer 17 in the sensor main body 13 at the same level as the output potential of the LPF 21. The potential is 3.3 v at the time of air-fuel ratio detection.

The reference voltage generating circuit 25 generates a reference voltage of 3.0 V by dividing a prescribed voltage Vcc. The second voltage-follower circuit 26 has the same circuit configuration as the first voltage-follower circuit 22, and maintains the potential of the exhaust-side electrode layer 16 in the sensor main body 13 at the reference voltage of 3.0 V. Accordingly, at the time of air-fuel ratio detection, a voltage V of 0.3 V is applied between the two electrode layers in the sensor main body 13, and thus the air-fuel ratio can be detected over a wide range by measuring the limiting current, as explained with reference to the characteristic diagram of FIG. 3. The resistor 23 in the first voltage-follower circuit 22 acts as the current detection circuit. Potential $V_0$ at the sensor-side terminal of the resistor 23 and potential $V_1$ at the other terminal are supplied to the CPU 40. The CPU 40 converts the analog potentials $V_0$ and $V_1$ at both ends of the resistor 23 into digital form, computes the potential difference "$V_1-V_0$" between both ends and, based on the potential difference and the resistance value of the resistor 23, computes a current I whose sign is positive when it flows in the direction from the first voltage-follower circuit 22 to the atmosphere-side electrode layer 17 in the sensor main body 13.

Figure 5:
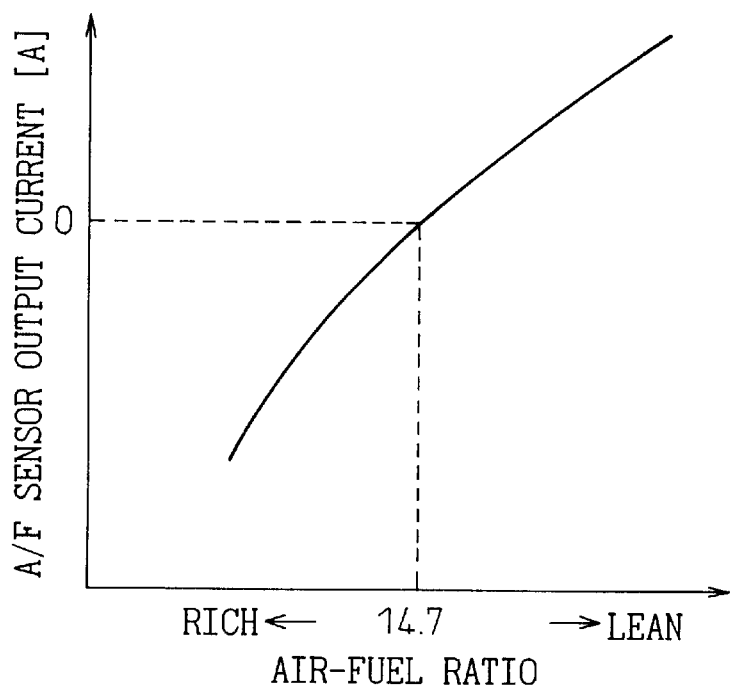
FIG. 5 is a characteristic diagram showing the relationship between the air-fuel ratio and the output current of the air-fuel ratio sensor.

As can be understood from the explanation given in connection with FIG. 3, the computed current value and the air-fuel ratio has the relationship such as shown in FIG. 5. As a result, the CPU 40 can determine the air-fuel ratio in the exhaust based on the detected current value, and hence can accomplish air-fuel ratio feedback control.

Figure 6:
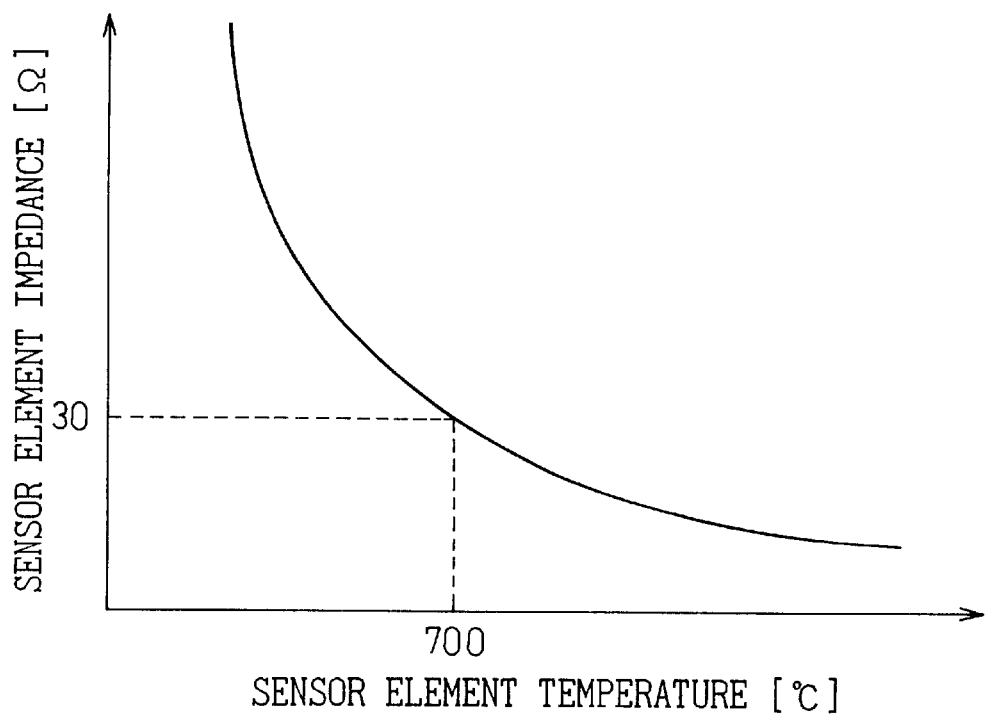
FIG. 6 is a characteristic diagram showing the relationship between element temperature and element impedance.

Here, to detect the air-fuel ratio, the sensor element (zirconia element) 14 must be maintained in the active state. The active state can be accomplished by maintaining the temperature of the element at a predetermined value, for example, 700° C. Since there is given correlation between the temperature and impedance of the element as shown in FIG. 6, if the temperature of the element is to be maintained at 700° C. the element should be controlled so as to exhibit an impedance of 30Ω. To achieve this, the impedance of the element is detected and, based on the detected impedance value, control is performed to maintain the element in the active state by feedback control of the heater driving circuit 30.

However, as previously described, as the sensor element degrades over time, the element impedance becomes higher for the same element temperature. As a result, when the sensor element has degraded, if feedback control of heater supply power is performed so that the detected value of the element impedance matches the target impedance, the element temperature may rise even when there is no degradation in the output characteristic and response of the air-fuel ratio sensor, and the sensor can be damaged. In view of this, the present invention detects the degree of degradation of the sensor element and, if degradation of the element is detected, limits the supply power to the heater to prevent the heater temperature and hence the element temperature from rising excessively.

Figure 7:
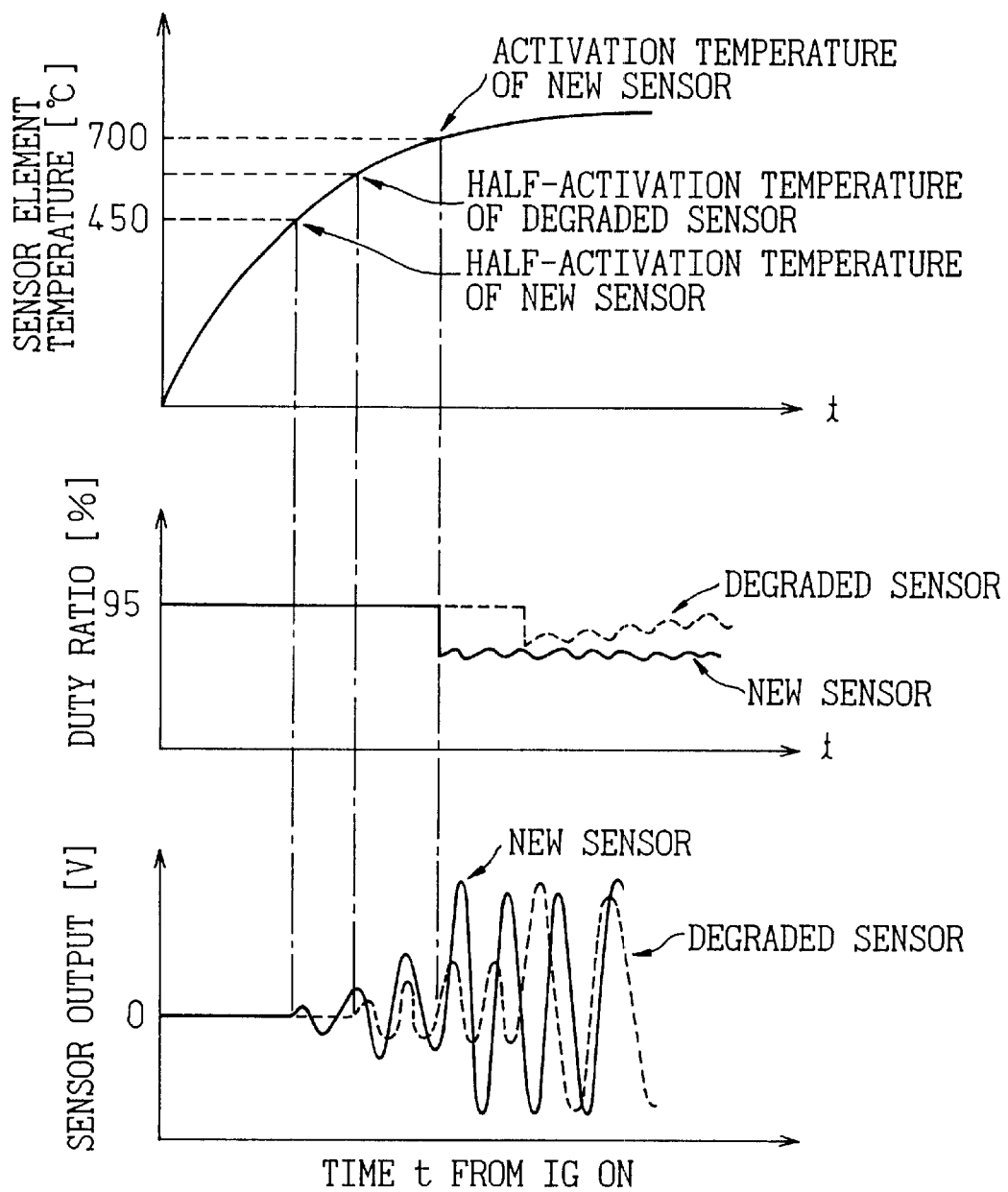

FIG. 7 is a time chart showing the variations of the element temperature, heater energization duty ratio, and sensor output with the elapsed time from the turning on of the ignition switch. In the present invention, to detect degradation in the sensor element, the sensor's half-activation time is detected during the engine start-up period before the feedback control based on the element impedance is performed. During the engine start-up, since the heater is nearly fully energized (for example, to 95% of the full energization), and since variations in heater resistance are small, the sensor element exhibits substantially the same temperature rise regardless of whether the sensor is degraded or not.

However, the half-activation temperature at which the sensor is activated and its output begins to change differs depending on the presence or absence of element degradation. More specifically, the length of the half-activation time from the moment the ignition switch is turned on to start energizing the heater toward the prescribed level to the moment the sensor is put in the half-active state increases as the element degrades. In view of this, in the present invention, the half-activation time is detected and, based on the detected half-activation time, an upper limit is set on the energization duty ratio for feedback control.

Figure 8:
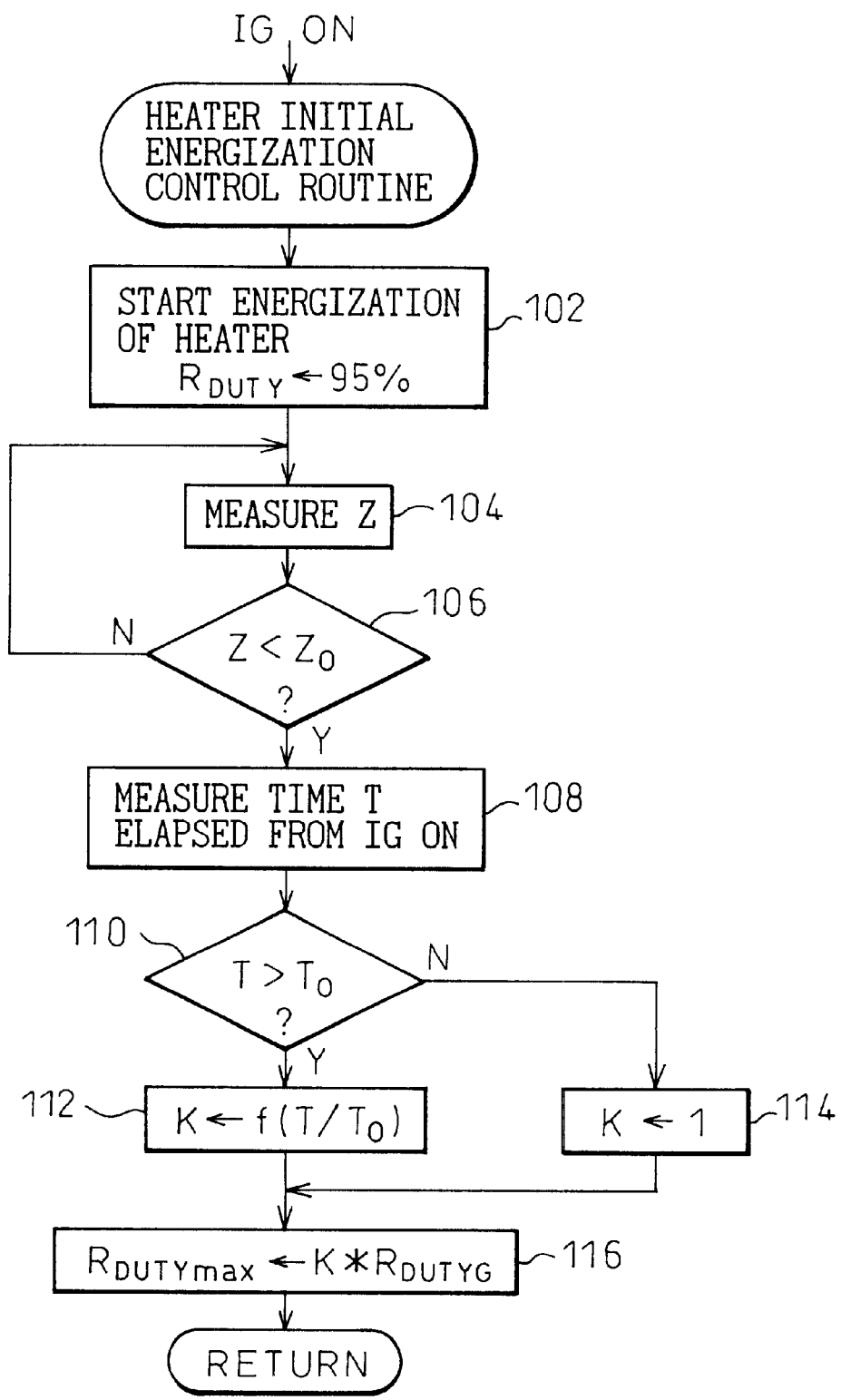
FIG. 8 is a flowchart illustrating a procedure for a heater initial energization control routine executed by a CPU.
Figure 9:
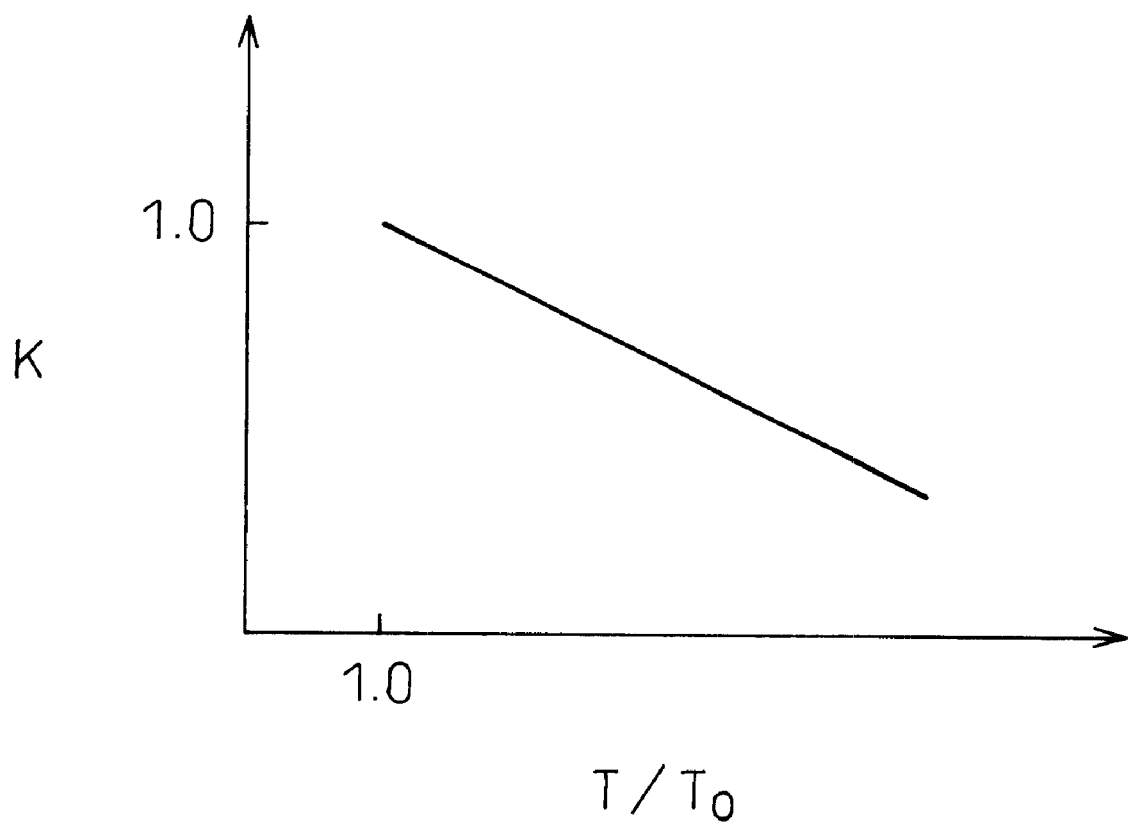
FIG. 9 is a diagram showing a map for obtaining a duty ratio upper limit correction coefficient K in accordance with a half-activation time ratio.

FIG. 8 is a flowchart illustrating a procedure for a heater initial energization control routine executed by the CPU 40. FIG. 9 is a map which is referred to during the execution of the heater initial energization control routine; this map is used to determine the duty ratio upper limit correction coefficient K in accordance with the half-activation time ratio (described later). The heater initial energization control routine shown in FIG. 8 is initiated when the ignition switch is turned on (IGON).

First, in step 102, energization of the heater 18 is started with the duty ratio $R_{DUTY}$ set to the predetermined value 95%. Next, in step 104, the present element impedance Z is measured. In step 106, the measured Z is compared with value $Z_0$ experimentally obtained in advance as the element impedance in the half-active state; if $Z \geq Z_0$, that is, if the half-active state is not reached yet, the process returns to step 104, while if $Z < Z_0$, if the half-active state is reached, the process proceeds to step 108.

In step 108, the time elapsed from the moment that the ignition switch is turned on (IGON) is measured as the half-activation time T. Next, in step 110, the measured half-activation time T is compared with the maximum half-activation time $T_0$ experimentally obtained in advance based on a normally operating sensor free from degradation. Then, if $T \leq T_0$, that is, if no degradation is detected in the element, the process proceeds to step 114 where the duty ratio upper limit correction coefficient K is set to 1.

On the other hand, if $T < T_0$, that is, if degradation is detected in the element, the process proceeds to step 112. In step 112, the duty ratio upper limit correction coefficient K corresponding to the half-activation time ratio $T/T_0$ is determined by referring to the map shown in FIG. 9. In the map of FIG. 9, as $T/T_0$ increases, the degree of degradation increases, and therefore the value of K decreases correspondingly.

In step 116, which is carried out after step 112 or 114, the duty ratio upper limit value $R_{DUTYmax}$ considering the sensor degradation is determined by performing the calculation $$R_{DUTYmax} \leftarrow K * R_{DUTYG}$$

where K is the duty ratio upper limit correction coefficient K and $R_{DUTYG}$ is the duty ratio guard value predetermined based on a normally operating sensor by a prior known control method.

Figure 10:
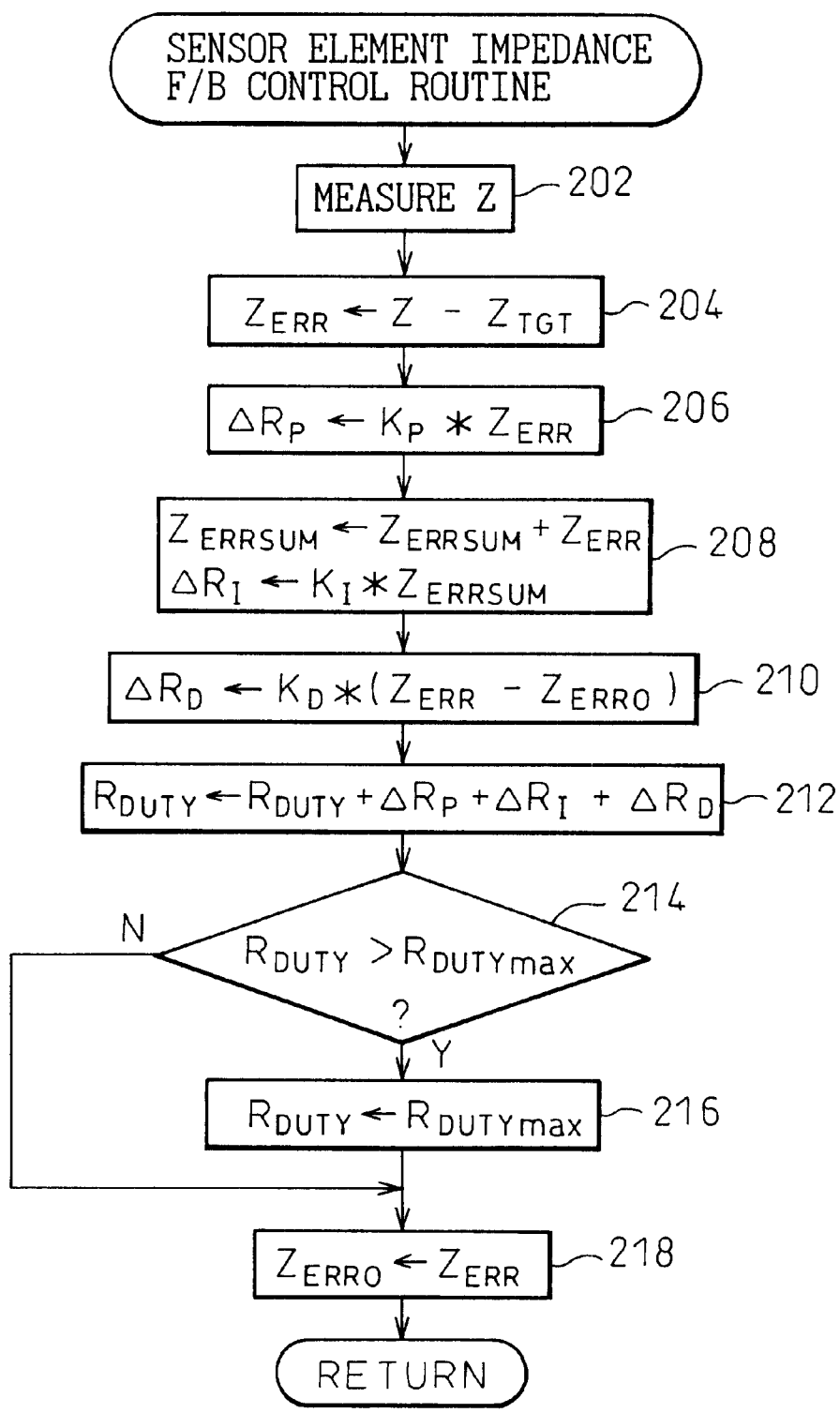
FIG. 10 is a flowchart illustrating a procedure for a sensor element impedance feedback heater control routine executed by the CPU.

FIG. 10 is a flowchart illustrating a procedure for a sensor element impedance feedback control routine executed by the CPU 40. This routine is executed at predetermined intervals of time after the activation of the sensor, and the duty ratio $R_{DUTY}$ to be supplied to the heater driving circuit 30 is determined based on the impedance of the sensor element. First, in step 202, the element impedance Z is measured. Next, in step 204, the deviation, $Z_{ERR}$, between the measured element impedance Z and the target element impedance $Z_{TGT}$ is calculated.

Then, in step 206, the proportional term $\Delta R_p$ in PID control is obtained by the calculation $$\Delta R_p \leftarrow K_p * Z_{EER}$$

where $K_p$ is the proportional gain. Next, in step 208, the deviation integrated value $Z_{ERRSUM}$ is updated by the calculation $$Z_{ERRSUM} \leftarrow Z_{ERRSUM} + Z_{ERR}$$

and the integral term $\Delta R_I$ in PID control is calculated by $$\Delta R_I \leftarrow K_I * Z_{ERRSUM}$$

wherein $K_I$ is the integral gain.

Next, in step 210, the derivative term $\Delta R_D$ in PID control is calculated by $$\Delta R_D \leftarrow K_D * (Z_{ERR} - Z_{ERR0})$$

where $K_D$ is the derivative gain, and $Z_{ERR0}$ is the deviation calculated when the routine was run the last time. Next, in step 212, the duty ratio $R_{DUTY}$ in PID control is determined by the calculation $$R_{DUTY} \leftarrow R_{DUTY} + \Delta R_p + \Delta R_I + \Delta R_D$$

Then, in steps 214 and 216, guard processing is performed so that the calculated $R_{DUTY}$ is limited to the duty ratio upper limit value $R_{DUTYmax}$ or less. More specifically, when $R_{DUTY} > R_{DUTYmax}$ in step 214, then in step 216 $R_{DUTYmax}$ is substituted for $R_{DUTY}$. In the final step 218, the calculated $Z_{ERR}$ is stored as $Z_{ERR0}$ to get ready for the next execution of the routine.

While the present invention has been described with reference to a specific embodiment thereof, it will be appreciated that the invention is not limited to the embodiment described herein. For example, though the above embodiment of the invention has been described by taking the so-called thimble-shaped air-fuel ratio sensor as an example, the invention is also applicable to the so-called planar-type air-fuel ratio sensor, and is not limited to any particular air-fuel ratio sensor structure.

As described above, according to the present invention, the element impedance of the air-fuel ratio sensor is detected, and the air-fuel ratio sensor is maintained in the active state by feeding back the detected impedance and thereby controlling the power to be supplied to the heater. According to the thus configured heater control device for the air-fuel ratio sensor, even when the sensor element has degraded, an excessive temperature rise in the heater and the sensor element can be suppressed and damage to the heater or the sensor element can be prevented, without providing any new devices.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A heater control device for an air-fuel ratio sensor, comprising:
    feedback control means for controlling supply power to a heater, based on element impedance of said air-fuel ratio sensor, for heating said air-fuel ratio sensor;
    half-activation time detection means for detecting half-activation time of said air-fuel ratio sensor; and
    power limiting means for limiting, based on the half-activation time detected by said half-activation time detection means, the power that is feedback-controlled by said feedback control means.

* * * * *